(12) United States Patent
Brandstaetter et al.

(10) Patent No.: US 7,726,863 B2
(45) Date of Patent: Jun. 1, 2010

(54) MEDICAL HANDLE DEVICE AND ILLUMINATION APPARATUS

(75) Inventors: Andreas Brandstaetter, St. Pantaleon (AT); Anton Schalda, Ostermiething (AT); Wolfgang Wendtner, Lamprechtshausen (AT)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 352 days.

(21) Appl. No.: 11/820,988

(22) Filed: Jun. 20, 2007

(65) Prior Publication Data

US 2008/0045802 A1 Feb. 21, 2008

(30) Foreign Application Priority Data

Jun. 22, 2006 (EP) .................................. 06012842
Jun. 6, 2007 (EP) .................................. 07011078

(51) Int. Cl.
*A61B 1/06* (2006.01)
(52) U.S. Cl. ................... 362/572; 362/119; 362/249.02; 362/311.02; 362/399; 362/581; 362/645; 362/804; 362/800
(58) Field of Classification Search ................. 362/249, 362/572–575, 577, 581, 119, 120, 645, 311.02, 362/311.15, 202, 399, 804
See application file for complete search history.

(56) References Cited

U.S. PATENT DOCUMENTS 2,761,057 A * 8/1956 Modell ........................ 374/191

| 3,109,238 | A | | 11/1963 | Marks |
| 4,295,152 | A | | 10/1981 | Khoe et al. |
| 4,779,173 | A | * | 10/1988 | Carr et al. .................... 362/109 |
| 5,139,421 | A | * | 8/1992 | Verderber .................... 433/31 |

(Continued)

FOREIGN PATENT DOCUMENTS

DE 193 59 501 A1 7/2005

(Continued)

OTHER PUBLICATIONS

European Search Report for EP07011078 (mailed Mar. 11, 2009).

*Primary Examiner*—Sandra L O'Shea
*Assistant Examiner*—Leah S Lovell
(74) *Attorney, Agent, or Firm*—Klarquist Sparkman, LLP (57) ABSTRACT

A medical handle device having an illumination apparatus with at least one optical semiconductor component and a method for manufacturing such a hand-held device are displayed. It is proposed that in order to adapt the hand-held device to the specific requirements of a medical application such as uniformly high light emission, high mechanical resistance, sterilizability and electric safety, the illumination apparatus is provided with a base body, at least one blind hole arranged in the base body, a light-emitting window which is formed by the part of the base body extending from the bottom of the blind hole to the first end of the base body and is connected to a cover device which is connected to the base body and with which the blind hole forms a hermetically sealed interior, whereby the at least one optical semiconductor component is arranged in the hermetically sealed interior and the base body and the cover device are made of an electrically non-conducting material that can withstand sterilization. In some embodiments, at least one optical semiconductor component is encased in a transparent thermoplastic material.

29 Claims, 5 Drawing Sheets

U.S. PATENT DOCUMENTS

| | | |
|---|---|---|
| 6,137,224 A | 10/2000 | Centofante |
| 7,055,991 B2 * | 6/2006 | Lin .................. 362/311.02 |
| 7,097,364 B2 * | 8/2006 | Wang ..................... 385/76 |
| 7,291,116 B2 * | 11/2007 | Kirchner ................ 600/553 |
| 7,581,854 B2 * | 9/2009 | Ford ................. 362/311.02 |
| 2008/0197376 A1 * | 8/2008 | Bert et al. ................ 257/99 |
| 2009/0097236 A1 * | 4/2009 | Miller et al. ........... 362/119 |

FOREIGN PATENT DOCUMENTS

| | | |
|---|---|---|
| DE | 10359501 | 7/2005 |
| EP | 1 093 765 A2 | 4/2001 |
| WO | 2004/107457 | 12/2004 |

* cited by examiner

MEDICAL HANDLE DEVICE AND ILLUMINATION APPARATUS

CROSS REFERENCE TO RELATED APPLICATIONS

The present application claims priority from pending European Patent Application No. 06012842.8, filed Jun. 22, 2006, and from pending European Patent Application No. 07011078.8, filed Jun. 6, 2007, which are both incorporated herein by reference.

BACKGROUND

1. Field

The present application relates to a hand-held medical handle device having an illumination apparatus with at least one optical semiconductor component as the light source and a method for manufacturing such a medical handle device.

2. Description of Prior Art

A hand-held medical device or medical handle device having an illumination apparatus with a light-emitting diode (LED) is known from the document EP 1,093,765 A2. The illumination apparatus consists of a holder with a U-shaped cross section in which the LEDs are held and are cast in a transparent heat-resistant synthetic resin. The synthetic resin, originally liquid, is cast into the holder, where it undergoes a chemical reaction, causing it to harden and cure, so that the LEDs are sealed off from the environment. Light emission and light conduction are accomplished through the cured synthetic resin. This design should achieve the result that the illumination apparatus can be sterilized in an autoclave.

However, the illumination apparatus of this medical handle device has many disadvantages. One disadvantage is that known synthetic resins suitable for this intended application undergo yellowing after repeated sterilization, so the light transmission and luminous efficiency deteriorate noticeably during the lifetime of the medical handle device. Another disadvantage is that the synthetic resins have a comparatively soft surface. Since the light is emitted through the synthetic resin, it is located at the surface of the illumination apparatus, and thus there is the risk of mechanical damage to the synthetic resin sheathing. Therefore, the release of light by the illumination apparatus is further exacerbated, e.g., due to scratching where the light is refracted or deflected. Furthermore, there is the risk that deep mechanical damage may lead to cracks extending to the LEDs, so that they are no longer protected from water vapor or chemicals, especially during sterilization. The front surface of the resin facing the treatment site may also be designed to be essentially only flat, so that further processing of the emitted light is impossible.

Furthermore, encapsulated LEDs are known from the state of the art, where their casing consists of at least one metallic component, often several metallic components, see, for example, U.S. Pat. No. 4,295,152. These encapsulated LEDs cannot be used in medical handle devices because they do not meet the requirements for electrical safety. If the medical handle devices can be connected to a power source, e.g., if they have an illumination apparatus or are operated with an electric motor, then it is essential to be sure that no electricity is transferred to the user or to the patient during operation or even when a defect occurs. If traditionally encapsulated LEDs having metallized components are used, then to maintain these specifications, defined distances must be stipulated between the electrically conducting metallic outer sheath of the medical handle device and voltage-carrying components such as the encapsulated LED. These defined distances will depend on various factors and amount to at least 0.4 mm (air gap) and/or 0.8 mm (creep zone), for example, in the case of a power supply of 2.8-3.5 V, which is required per LED; in the case of medical handle devices that carry water, e.g., to deliver a spray of water, the distance must be 1.6 mm (air gap) and/or 3.4 mm (creep zone). Since the diameter of the medical handle device is comparatively small at approximately 1-2 cm, it is often impossible to meet these requirements, so that encapsulated LEDs having metal sheaths known in the state of the art cannot be used for medical handle devices.

Therefore, the object is to create a medical handle device having an illumination apparatus that does not have the disadvantages mentioned above. The hand-held device should have in particular an illumination apparatus which guarantees an improved emission of light, preferably as uniform as possible, over the entire lifetime of the hand-held device, which has a surface that can better withstand mechanical damage in particular, which can be sterilized, which allows processing of the light emitted and which fulfills the requirements for electrical safety.

Another disadvantage of the illumination apparatus known from document EP 1,093,765 A2 is the need to make available a separate holder for each illumination apparatus into which the synthetic resin is cast. This is an obstacle in manufacturing the illumination apparatus and increases the manufacturing expense as well as storage and production costs. However, the holder is absolutely necessary because the chemical curing reaction of the synthetic resin takes place very slowly and the holder serves to shape and store the synthetic resin and to hold the LEDs during the liquid phase of the synthetic resin until its final hardening. Since the synthetic resin adheres to the holder, it cannot be released from the cured resin compound or it can be released only at considerable effort, e.g., by first applying a coating to the walls of the holder, so that the holder is usually installed together with or as a part of the illumination apparatus.

Another object is therefore to create a method for manufacturing a mechanical hand-held device having an illumination apparatus and a medical handle device having an illumination apparatus that does not have the disadvantages mentioned above. The hand-held device should have an illumination apparatus which is simpler and less expensive to manufacture, i.e., in particular it should not be necessary to provide a separate holder for each illumination apparatus, into which the optical semiconductor components or LEDs as well as the casting compound encasing them are to be introduced. The hand-held device and the illumination apparatus should also be sterilizable and the light transmission through the illumination apparatus and the light yield should also remain as uniform as possible even after repeated sterilization.

SUMMARY

The design according to one exemplary embodiment of the illumination apparatus of the hand-held device having a base body and at least one blind hole arranged in the wall of the base body and a light-emitting window that is formed by the part of the wall extending from the bottom of the blind hole to the first end of the base body has the advantage that a surface facing the treatment site is thereby created, a surface which can better resist mechanical damage. Furthermore, the surface offers a simple option for processing the light emitted by the optical semiconductor element in which the surface of the base body is formed as a planar polished surface or as an optical element, e.g., as a concave or convex lens. An optical element preferably designed in one piece with the base body has the additional advantage that it need not be attached to the illumination apparatus and therefore there is no danger that it will lift off or separate from the illumination apparatus, e.g., due to the ambient conditions prevailing during sterilization, and thus providing an opportunity for growth of microorganisms in an interspace thereby formed or even becoming completely detached. An optical fiber can also be connected easily to the surface.

The at least one blind hole may have various forms; for example, it may be an essentially cylindrical hollow space or cavity that is only insignificantly larger than an optical semiconductor component accommodated therein, wherein a plurality of these cavities may be distributed uniformly or irregularly in the wall of the base body. Alternatively, the blind hole may also be designed to be larger, e.g., have an arcuated shape and may extend around the longitudinal axis of the base body, in which case again a plurality of blind holes, e.g., two quarter circular-shaped blind holes, may also be provided. Finally, the blind hole may also be designed as a continuous ring running around the longitudinal axis of the base body. If the blind hold is designed so that it may accommodate a plurality of optical semiconductor components, then an especially high light intensity can be achieved in a very small area.

The base body is made of an electrically nonconducting material capable of withstanding repeated sterilization. Furthermore, the light-emitting window must be transparent for the wavelength emitted by the at least one optical semiconductor component or for a spectrum created by a color conversion material arranged in the illumination apparatus. Preferred materials for the base body and the light-emitting window include synthetic or plastic materials, in particular thermoplastics, e.g., polyphenylsulfones, polyethersulfones, polycarbonates or polyamides, or glass. These materials are also electrically insulating, so that electrical safety is guaranteed. The preferred material for the base body is partially crystalline polyamides which are marketed in various embodiments as a molding compound, e.g., under the brand name Trogamid® by the company Degussa AG in Germany. These partially crystalline polyamides are also especially scratch-resistant and abrasion-resistant, so they can withstand mechanical stresses well.

In a first embodiment, the cover device that can be connected to the base body may be formed by at least one casting material, in particular synthetic resins such as epoxy resin, silicone resin or polyamide resins. This embodiment is very simple and inexpensive to produce. It also allows the arrangement and hermetic sealing of a plurality of optical semiconductors, optionally different ones, each in its own blind hole, whereby the arrangement of optical semiconductor components is especially preferably irregular, so that special light distribution patterns can be implemented. In this embodiment, at least a portion of the casting compound may be accommodated in the blind hole.

In a second exemplary embodiment, the cover device comprises at least one closure body, which is preferably cylindrical, rod-shaped, tubular or plate-shaped. The cover device is preferably made of a plastic, especially a thermoplastic, e.g., polyphenylsulfone, polyethersulfone, polycarbonate or polyamide, glass or ceramic. These materials, like the casting materials listed above, provide electric insulation so that electric safety is guaranteed. Partially crystalline polyamides are the preferred material for the base body and are offered, e.g., in various embodiments as a molding compound under the brand name Trogamid® by the company Degussa AG, Germany. The advantage of this second exemplary embodiment lies mainly in the very reliable connection that can be established between the cover device and the base body, in particular by laser welding, so that an extremely permanent seal of the interior in which the at least one optical semiconductor element is accommodated can be established. As also described in greater detail below, it is also possible to achieve very reliably a sealing of electric contacts which are optionally also provided for the electric power supply for the optical semiconductor component in the presence of a closure body.

It is not obligatorily necessary for the closure body of the cover device and the base body to be made of the same material. Preferably the different materials should have a similar or at least approximately the same thermal expansion coefficient, however, so that on heating of the illumination apparatus during sterilization in particular no cracks or leakage between the two components occur through which water vapor, chemicals or other contaminants can enter. The closure body of the cover device and the base body, however, are especially preferably made of the same materials in order to achieve the greatest possible sealing effect.

The base body may be joined to the cover device by welding, e.g., by ultrasonic welding or laser welding, by pressing, bonding or by means of sealing elements, e.g., O-rings or rubber rings. The laser direct welding method is preferably used; in this method one of the two components to be joined is transparent for the laser radiation while the other component absorbs the laser radiation. Due to the absorbed radiation, this component melts at the surface and transfers a portion of the heat to the transparent component, which also melts at the surface so that in the area of the contacting surfaces, the two components are joined as they cool subsequently. The two components are advantageously made of the same material for the use of this method.

If the base body and the cover device are made of plastic, then they may be manufactured by cutting from a workpiece or preferably by injection molding.

In a first exemplary embodiment, the electric supply device includes at least one first and one second electric contact for the electric power supply to the at least one optical semiconductor component. The contacts may be made of contact pins or flexible leads, for example. If there are several semiconductor components, they may be arranged in series or in parallel so that multiple electric contacts are provided accordingly. The connection between the at least one LED and the electric contacts may be accomplished by means of bonding wires or by printed circuit board conductors, for example.

If the cover device is formed by at least one casting material, then preferably the electric contacts are first connected to the at least one LED, introduced at least partially into the blind hole and then cast in place there. Alternatively, it is also possible for the contacts not to pass through the casting material but instead through bores in the base body, in which case the sealing is achieved in the same way as that described below for a closure body of a cover device.

If the cover device includes at least one closure body, then the at least two electric contacts are passed through bores either in the closure body or in the base body, in which case the bores extend into the blind hole/the hermetically sealed interior. The sealing of the electric contacts may in turn be accomplished by welding, e.g., by ultrasonic welding or laser welding, pressing, bonding or by means of sealing elements. The closure body or the base body, however, is preferably produced by injection molding, in which case the electric contacts are introduced into the injection mold prior to the start of production by injection molding and they are thus injection molded together, thereby achieving an extremely reliable seal.

In a second exemplary embodiment, an inductive electric supply device is provided for the power supply to the at least one optical semiconductor component, having at least one first coil which is arranged in the hermetically sealed interior of the illumination apparatus, and at least one second coil which is arranged outside of the hermetically sealed interior. Preferably additional electronic components, e.g., rectifiers, current regulators, AC-DC converters, capacitors or resistors are also provided between the first coil and the at least one optical semiconductor component in order to supply the at least one optical semiconductor component with the required d.c. voltage and/or to ensure a constant power supply. If the use of these electronic components is impossible owing to lack of space, then the inductive supply device may be operated above the so-called flicker frequency (corresponding to approximately 25 Hz a.c. voltage), so that the resulting impression for the human eye is that of a constant uninterrupted light emission of the at least one optical semiconductor component.

A method for producing a medical handle device having an illumination apparatus comprises:
  providing a medical handle device,
  providing an illumination apparatus having at least one optical semiconductor component as the light source, whereby the illumination apparatus additionally comprises:
    a base body having a first end and a second end,
    at least one blind hole arranged in the base body, extending from the second end of the base body in the direction of the first end,
    a light-emitting window formed by the part of the base body extending from the bottom of the blind hole to the first end of the base body,
    a cover device that is connectable to the base body and forms a hermetically sealed interior with the blind hole,
    wherein the optical semiconductor component is arranged in the hermetically sealed interior and is connected or can be connected via an electric power supply device to a power source and whereby the base body and the cover device are made of an electrically nonconducting material,
  fastening the illumination apparatus in or on the medical handle device.

Another method for producing a medical handle device with an illumination apparatus comprises the following:
  providing a medical handle device,
  providing at least one optical semiconductor component designed as a radiation source,
  enclosing the at least one optical semiconductor component in a transparent thermoplastic and
  fastening the at least one encased optical semiconductor component in or on the medical handle device.

By encasing or encapsulating the at least one optical semiconductor component with a transparent thermoplastic, this eliminates the need for manufacturing, storing and installing a separate holder for each illumination device. If the at least one optical semiconductor component is encased, e.g., in a liquid thermoplastic, as described in greater detail below, said thermoplastic being added to a mold in which the optical semiconductor component is situated, then the curing process of the thermoplastic proceeds many times more rapidly than it does with a synthetic resin because the curing process is achieved not by a chemical reaction but instead by a cooling process. The curing of the thermoplastic thus takes place within acceptable periods of time, in particular with regard to technical production and economic aspects, and specifically such short periods of time that at least an adequate progress in the curing process can be expected and then the at least one optical semiconductor component encased in the thermoplastic can be removed from the mold. Since there is little or no adhesion of the cooled thermoplastic to the mold, which is usually made of metal, the removal from the mold can therefore be performed with no problem. The mold may then be used to produce a large number of casings.

The optical semiconductor component is thus arranged and/or inserted directly in the thermoplastic, wherein the thermoplastic and/or the uninstalled illumination apparatus no longer has a holder for holding the thermoplastic after the end of the encasing procedure and after its release from the mold. With the use of the thermoplastic, the illumination apparatus also fulfills specifications regarding electric safety, in particular preventing any electric current from being transferred to the user or to the patient during operation or even when a defect occurs.

The optical semiconductor component encased in the transparent thermoplastic is preferably designed as a semiconductor chip which is part of an illumination element, in particular, e.g., a light-emitting diode (LED). The light-emitting diode may in turn comprise additional components, e.g., protective casings for the semiconductor chip or conversion material for converting the wavelength emitted by the at least one optical semiconductor element. The illumination apparatus is equipped with at least one optical semiconductor component, but several optical semiconductor components connected electrically in series or in parallel may of course also be provided.

Encasing the at least one optical semiconductor component in a transparent thermoplastic comprises complete inclusion of the optical semiconductor component in the plastic compound as well as just partial enclosing of the optical semiconductor component. The thermoplastic may also come into direct contact with at least one optical semiconductor component as well as being arranged at a space from it. Various transparent thermoplastics are suitable for encasing the component, e.g., propylene random copolymers (PPR), polycarbonates (PC), polymethylenepentene (PMP), cyclooleofin copolymers (COC) or polyphenylsulfone (PPSU). In addition to their high transparency, these plastics have a good UV stability, a low tendency to discolor or turn yellow and a high chemical stability, especially with respect to water vapor and disinfectants, cleaning and maintenance products. They can thus be exposed to repeated sterilization, disinfection, cleaning and care treatments as well as being usable for medical applications, in particular dental applications.

In one exemplary embodiment, the at least one optical semiconductor component is encased by providing a solid thermoplastic material, preferably in the form of granules or a powder, then liquefying the thermoplastic and curing the thermoplastic. The advantage of this exemplary embodiment is that in encasing the at least one optical semiconductor component, no other changes in the plastic are necessary except for a change in the physical state. In particular, no chemical reactions take place during curing so that the risk of incomplete curing and the associated development of cracks and leakage can be greatly reduced. This also makes the encasing time and curing much shorter when using thermoplastic materials in comparison with using synthetic resins.

In particular the encasing of the at least one optical semiconductor component and thus the change in the aggregate state is achieved by heating of the thermoplastic material, preferably to temperatures of maximally approximately 310° C., especially preferably to temperatures of maximally approximately 280° C. If these temperature limits are upheld, damage to the optical semiconductor components during the encasing process due to excessive thermal stress is prevented.

To obtain a defined shape of the plastic casing of the optical semiconductor component or the illumination apparatus, in another exemplary embodiment, before encasing the at least one optical semiconductor component in the thermoplastic, the at least one optical semiconductor component is arranged in a mold and then the thermoplastic material is introduced into the mold. The mold here is of such a design that different elements are provided on the outsides of the casing, e.g., fastening elements in the form of plug parts for fastening the illumination apparatus to the hand-held device or optical elements, e.g., lenses on the light-emitting window. Additionally or alternatively, the mold is such that function elements are formed in the interior of the plastic casing, e.g., bores, blind holes, receptacles or connecting elements or closure elements. The casing of the optical semiconductor component is preferably in the form of a ring or hollow cylinder, so that a component, e.g., a shaft, axle or tool can be inserted through the central bore.

To guarantee uniform and complete filling of the mold with the thermoplastic material, the liquefied plastic is preferably injected into the mold under pressure.

In another exemplary embodiment, the at least one optical semiconductor component is encased by the thermoplastic material in such a way that the thermoplastic material either comes in direct contact with at least the radiation-emitting surface of the at least one optical semiconductor component or it comes in contact with parts connected to the radiation-emitting surface. This yields an effective means of conducting the emitted radiation with the lowest possible loss and with a small number of media or material transitions to be overcome by the radiation.

In another exemplary embodiment, the illumination apparatus additionally comprises a carrier for the at least one optical semiconductor component, in particular a circuit board or a multilayer ceramic, and an electric power supply unit for supplying power to the at least one optical semiconductor component, whereby carrier and the electric power supply device are encased at least partially by the thermoplastic material. Due to this embodiment, the production of the illumination apparatus and its assembly are facilitated in particular. Preferably the carrier and at least parts of the electric power supply device are first connected to each other and then encased by the thermoplastic material. Preferably a plurality of optical semiconductor components or LEDs are arranged on the carrier. The carrier is especially preferably designed in a ring shape so that a tool can be passed through its central bore and it can thus be arranged on the tool end of the hand-held device element around the tool holder or the tool.

The design of the illumination apparatus of the hand-held device according to one exemplary embodiment with a base body and at least one receptacle arranged in the base body, e.g., in its wall and a light-emitting window that is formed by the part of the wall that extends from the receptacle to the first end of the base body, has the advantage that a surface facing the treatment site is created such that the surface can better withstand mechanical damage than the soft synthetic resin. In addition, the surface offers a simple possibility of processing the light emitted by the optical semiconductor component in which the surface of the base body is formed as a planar polished surface or as an optical element, e.g., as a concave or convex lens. An optical element which is preferably designed in one piece with the base body has the additional advantage that it need not be attached to the illumination apparatus and therefore there is no risk that it will become detached or completely separated from the illumination apparatus due to the ambient conditions prevailing during sterilization in particular and it does not offer the opportunity for growth of microorganisms in the resulting interspace. An optical fiber may also be connected to the surface in a simple manner.

The at least one receptacle may have various shapes; for example, it may be an essentially cylindrical hollow space or cavity which is only insignificantly larger than an optical semiconductor component arranged therein, whereby a plurality of these hollow spaces may be distributed uniformly or irregularly in the base body or in the wall of the base body. As an alternative, the receptacle may also be designed to be larger, e.g., in the form of an arc of a circle, and may extend around the longitudinal axis of the base body, in which case there may also be a plurality of receptacles, e.g., two receptacles in the form of a quarter circle. Finally, the receptacle may also be designed as a continuous ring running around the longitudinal axis of the base body. If the receptacle is designed so that it accommodates a plurality of optical semiconductor components, then a particularly high light intensity can be achieved with it on a small area.

Since the base body is made of a thermoplastic material, it is not electrically conducting. In addition, the light-emitting window must be transparent for the wavelength emitted by the at least one optical semiconductor component or for the spectrum generated by the color conversion material arranged in the illumination apparatus.

In a first embodiment, the cover device that can be connected to the base body may be formed by at least one casting material, in particular a synthetic resin such as epoxy resin, silicone resins or polyamide resins. This embodiment is very simple and inexpensive to manufacture. It also allows a plurality of optical semiconductor components, optionally different components, to be arranged in its own suitable receptacle and hermetically sealed therein, in which case the arrangement of optical semiconductor components is especially preferably irregular so that special light distribution patterns can be implemented. In this embodiment, at least a portion of the casting compound may be accommodated in the receptacle.

In a second embodiment, the cover device comprises at least one closure body which preferably has a cylindrical, ring, tubular, rod or plate shape. The cover device is made of plastic, for example, especially thermoplastic, e.g., polyphenylsulfone, polyethersulfone, polycarbonate or polyamide, or glass or ceramic. The carrier may also serve as a cover device for the LEDs. The base body may be connected to the cover device by welding, e.g., by ultrasonic welding or laser welding, pressing, bonding or by means of sealing elements, e.g., O-rings or rubber rings. The laser transmission welding method is preferably used in which one of the two parts to be joined is transparent for the laser radiation while the other part absorbs the laser radiation. Due to the absorbed radiation, this part melts at the surface and transmits a portion of the heat to the transparent component, which also melts at the surface so that the two components are joined in the area of the mutually contacting surfaces in the subsequent cooling. The two components are advantageously made of the same material for the application of this method.

However, the cover device like the base body is preferentially also made of a thermoplastic material, e.g., random propylene copolymers (PPR), polycarbonates (PC), polymethylenepentene (PMP), cyclooleofin copolymers (COC) or polyphenylsulfone (PPSU). If the base body and the cover device are designed in two parts, they may be joined to one another by welding, bonding, pressing, melting or by means of sealing selects. The cover device and the base body are especially preferably designed as a one-piece casing, so that no additional connection between the two components is necessary, thus yielding an especially high sealing effect for the at least one optical semiconductor component. The base body and the cover device are preferably produced by injection molding in this one-piece embodiment.

As already indicated, it is not obligatorily necessary for the closure body of the cover device and the base body to be made of the same materials. If different materials are used, however, they should have a similar or approximately similar thermal expansion coefficient so that no cracks or leakage develop between the two parts especially when heating the illumination apparatus during sterilization, which would thus allow water vapor, chemicals or other soiling to penetrate into the parts.

The optical semiconductor component according to the various embodiments disclosed here is preferably designed as a semiconductor chip which is part of an illumination element in particular, e.g., a light-emitting diode (LED). The at least one optical semiconductor component or the LED is arranged on a carrier, e.g., a circuit board or a multilayer ceramic. However, they are preferably inserted directly into the blind hole or into the receptacle without a carrier and then encapsulated or cast therein or hermetically sealed by a cover part. This embodiment has the advantage of an especially low installed height and thus an especially low requirement for space in or on the hand-held device.

In a first exemplary embodiment, the electric power supply device includes at least one first and second electric contact for supplying power to the at least one optical semiconductor component. The contacts may be formed from contact pins or a flexible cord, for example. If there are multiple semiconductor components, they may be arranged in series or in parallel, so that there are multiple electric contacts accordingly. The connection between the at least one optical semiconductor component and the electric contacts can be established by bonding wires or by circuit board printed conductors.

If the cover device is formed by at least one casting material, then the electric contacts are preferably connected first to the at least one optical semiconductor component, introduced at least partially into the receptacle and then cast in place there. As an alternative, it is also possible for the contacts not to pass through the casting material but instead to pass through the base body, in which case the seal is accomplished in the same way as described below for a closure body of a cover device.

If the casing and/or the cover device comprises at least one base body and one closure body, then the at least two electric contacts are passed through bores either in the closure body or in the base body, in which case the bores extend into the receptacle/the hermetically sealed interior. The sealing of the electric contacts may in turn be accomplished by welding, e.g., ultrasonic welding or laser welding, pressing, bonding or by means of sealing elements.

If the casing, i.e., the cover device and the base body, is designed in one piece, then the at least one optical semiconductor component is connected to the electric contacts before being encased, and then the optical semiconductor component is surrounded with the thermoplastic material. The closure body or base body is preferably produced by injection molding, with the electric contacts being introduced into the injection mold before the start of injection molding production and also cast in place there so that they are accommodated in the thermoplastic material in bores or channels that correspond exactly to the diameter of the contacts, thus achieving an extremely reliable seal.

In a second exemplary embodiment, an inductive electric power supply device is provided for supplying electric power to the at least one optical semiconductor component, having at least one first coil which is arranged in the hermetically sealed interior of the illumination apparatus and at least one second coil which is arranged outside of the hermetically sealed interior. Preferably additional electronic components such as rectifiers, current regulators, AC-DC converters, capacitors or resistors are provided between the first coil and the at least one optical semiconductor component to supply the required d.c. voltage to the at least one optical semiconductor component and/or to ensure a constant electric power supply. If use of these electronic components is impossible because of the tight space conditions, then the inductive power supply device may be operated above the so-called flicker frequency (corresponding to approximately 25 Hz a.c. voltage), so that for the human eye this gives the impression of a constant uninterrupted emission of light by the at least one optical semiconductor component.

A battery or the electric power network may serve as the primary power source to which the electric contacts or the inductive power supply of the various illumination apparatuses disclosed is or can be connected. The electric power made available by the aforementioned power sources may be processed by means of electronic or electric components in accordance with the requirements of the semiconductor components.

In a preferred exemplary embodiment, the various illumination apparatuses disclosed are designed as ring lights, preferably mounted very close to or directly around the tool holder or the tool. Thus no optical light guide is required to conduct the light through the hand-held device to the tool end of the hand-held device, thereby greatly reducing radiation losses. With the illumination apparatuses designed as ring lights, at least the base body or the one-piece casing, optionally also the carrier and the cover device, have a bore which can hold the tool or the tool holder or through which they can be passed.

In another exemplary embodiment, the casing of the illumination apparatus or the base body and/or the cover device is/are made of a sterilizable plastic or preferably thermoplastic material, in particular a (thermo)plastic material having a resoftening point of more than 120° C. For all the embodiments of the hand-held device described and claimed here, the terms "material resistant to repeated sterilization," "sterilizable material" or "sterilizable plastic" are understood to refer to any material that does not show any significant changes or damage even after repeated introduction into an aggressive medium at a temperature of at least 120° C., preferably 130° C., especially preferably 134° C. and does not suffer any significant changes or damage when exposed to water vapor and/or in an environment with chemicals, in particular disinfectants, so that an interior space that is hermetically encased in such a material and sealed from the environment will remain hermetically sealed even after repeatedly introducing this material into this aggressive environment. Components accommodated in the interior, in particular semiconductor components, are thus protected from water vapor, chemicals, particles, lubricants or other contaminants by encapsulation with such a material during the sterilization process and also thereafter, and they can thus maintain their functionality. In particular the term "sterilizable material" or "sterilizable (thermo)plastic" is understood to refer to any material or plastic having a melting point or a resoftening point higher than 120° C.

The illumination apparatuses described here may be fastened to the outside of the medical handle device, e.g., by means of a plug or clamp connection. The illumination apparatus is preferably arranged in the interior of the hand-held devices, e.g., by means of plug or clamp connection or by bonding, where it is less disturbing for the user. The illumination apparatuses are preferably arranged around the tool holder or the tool, e.g., a rotary drill, a reciprocating file, a saw or a dental vibrating calculus-removing tool so that a high-intensity illumination free of shadows is obtained as close as possible to the treatment site. In this case the illumination apparatuses are arranged at least partially in the interior of the hand-held device, whereby the surface of the light-emitting window at the same time also forms the front end or a side border of the hand-held device.

The illumination apparatuses described here are used primarily for illumination of a preparation site and/or a tool that is driven by the hand-held device with visible light. As an alternative or in addition, however, the illumination apparatus may also be used for therapeutic or diagnostic applications, e.g., for curing photosensitive material, in particular filling material for dental cavities, for bleaching teeth or for detection of decayed dental tissue. In this case, optical semiconductor components or LEDs that emit a wavelength suitable for the particular application, which may also be outside of the visible light spectrum, are used.

The present invention is explained in greater detail below on the basis of preferred exemplary embodiments and with reference to the accompanying drawings:

DETAILED DESCRIPTION

Figure 4:
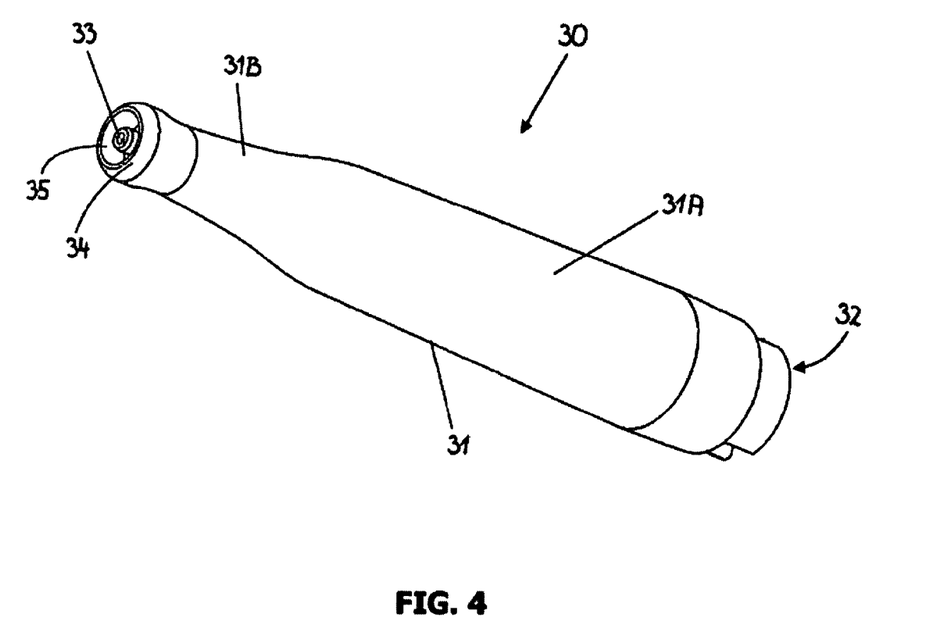
FIG. 4 shows a medical handle device in the form of a dental calculus-removing device.

FIG. 4 shows a dental calculus-removing device, often known as a scaler, as an example of a medical handle device 30. Of course, the term medical handle device is not limited to scalers, but also includes all other hand-held devices that can be used medically, surgically, orthopedically, dentally or cosmetically, in particular medical handle devices that are curved or have sections that are arranged at an angle to one another, medical handle devices having different drives or drive powers, e.g., hand-held devices operated with compressed air, water or electricity, medical handle devices having different tools such as drills, saws, millers, brushes, prophy cups, reamers, shavers, etc., medical handle devices for dispensing laser radiation or medical handle devices whose primary job is to emit light for illumination or for diagnostic, therapeutic or prophylactic treatment. The term hand-held device or medical handle device is also understood to include parts of such hand-held devices or medical handle devices and components such as motors, couplings, adapters or intermediate pieces for connecting components of a medical instrument.

The scaler comprises an elongated cylindrical outer sheath 31 that is hollow on the inside and is subdivided into a handle part 31A and a head part 31B. Various function parts may be arranged in the interior of the outer sheath 31 and may include, for example, a drive unit, lines for driving media and/or cooling media, vibration damping components, regulating and adjusting devices, etc. A connection device 32 for connecting the medical handle device 30 to a power source, e.g., to a source of compressed air or electricity, to one or more cooling media sources and optionally to a control unit, is provided on the end of the handle part 31A opposite the head part 31B. Since the connection device 32 and/or the various types of connection devices that can be used with such a medical handle device 30 are known, they will not be discussed further here.

Figure 1:
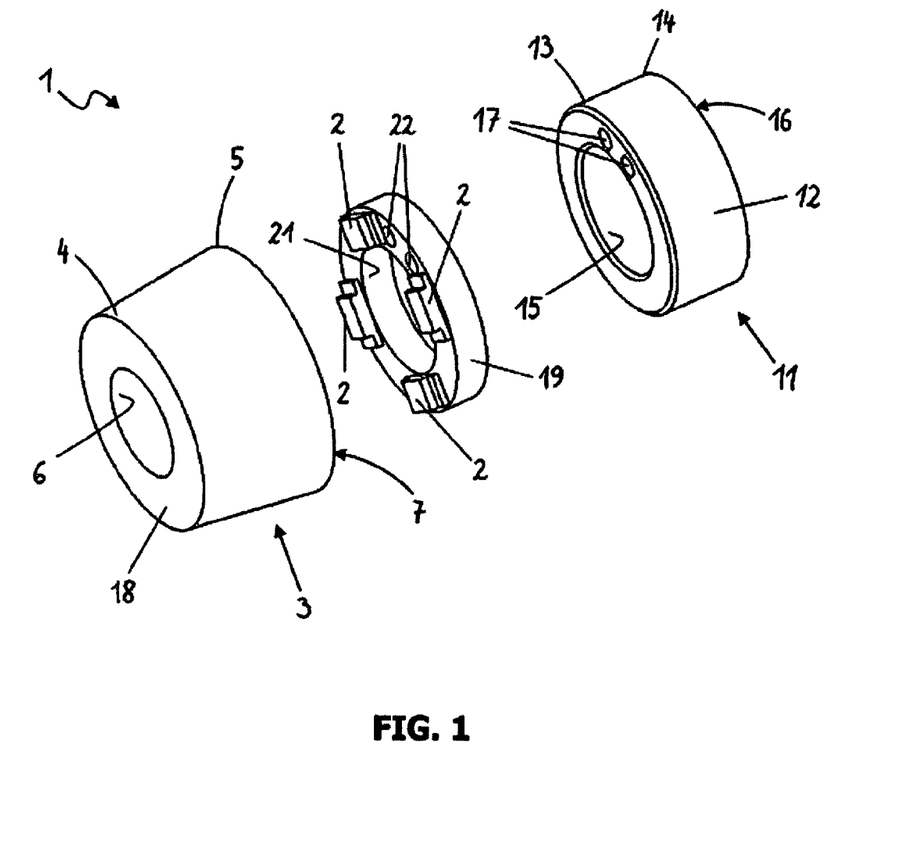
FIG. 1 shows an exploded diagram of a first exemplary embodiment of the illumination apparatus of a medical handle device.
Figure 2:
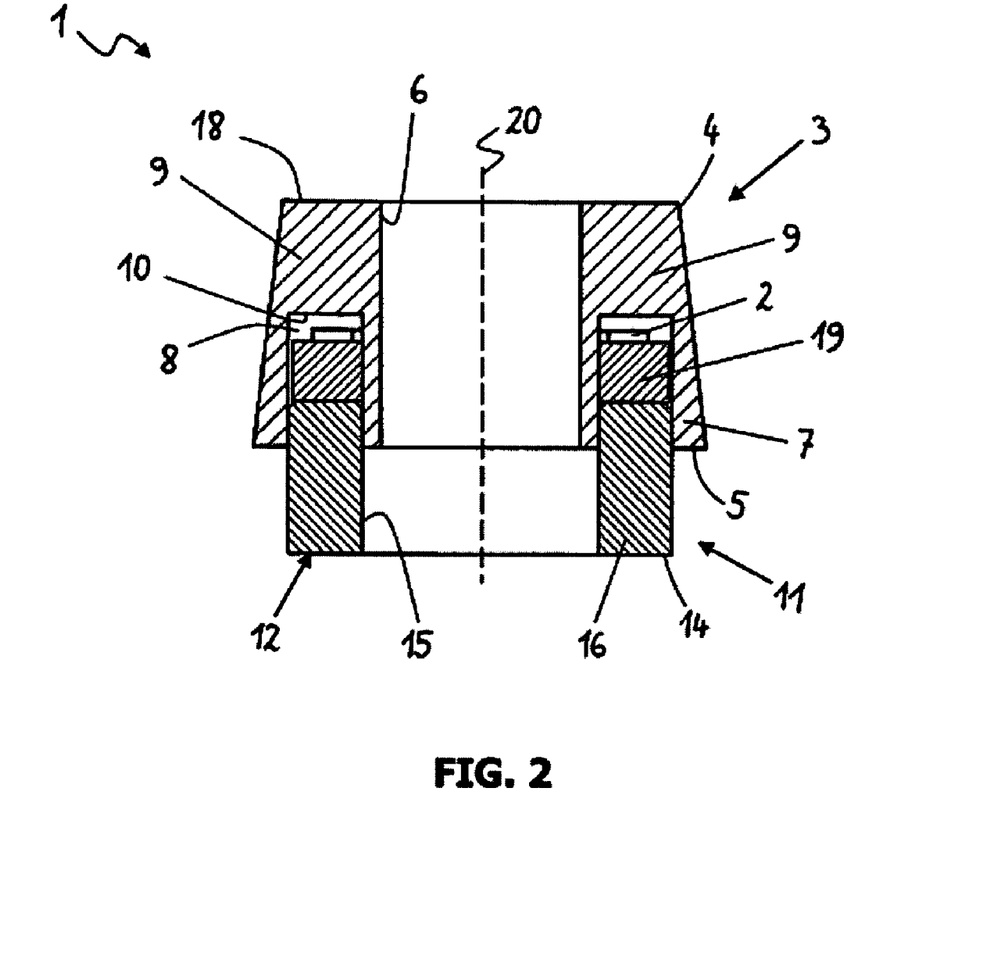
FIG. 2 shows a longitudinal section through the assembled illumination apparatus according to FIG. 1.
Figure 3:
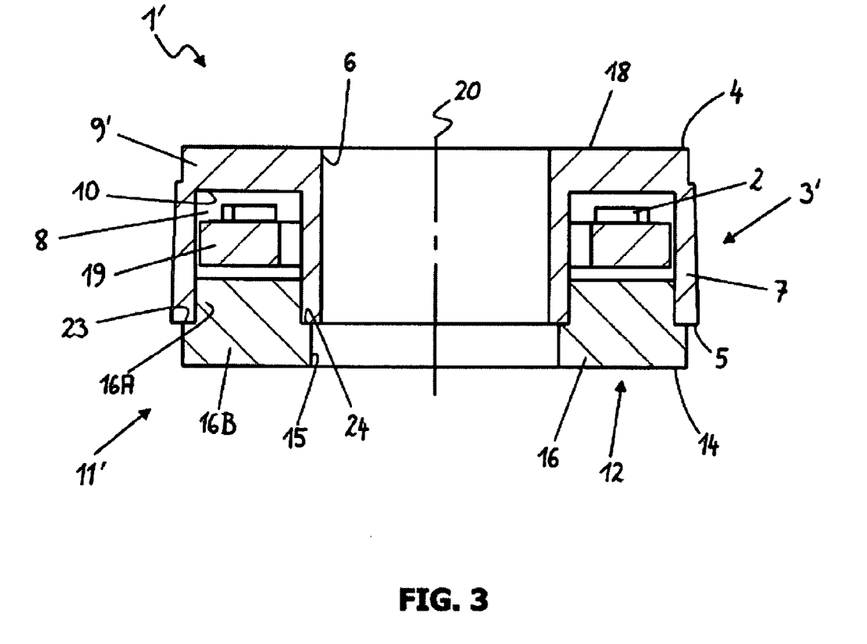
FIG. 3 shows a second exemplary embodiment of the illumination apparatus of a medical handle device.

A tool receptacle or tool holder 33 in the form of a hollow shaft having an inside thread into which the treatment tool can be screwed is provided on the distal end of the head part 31B. The tool receptacle 33 is surrounded by the sleeve-shaped cylindrical front end 34 of the head part 31B, where the cylindrical front end 34 is at a distance from the tool receptacle 33, thus forming a hollow space 35. An illumination apparatus 1 designed as a ring light can be inserted into this hollow space 35, as illustrated in FIGS. 1 through 3, for example. The illumination apparatus 1 is thus essentially accommodated in the medical handle device 30, whereby the light-emitting surface 18 is approximately flush with the front end 34. The tool receptacle 33 protrudes into or through one or more boreholes 6, 15 in the illumination apparatus 1, so that it is freely accessible for the user who can then insert the treatment tool into the tool receptacle 33 or release it from the tool receptacle with no problem.

According to FIGS. 1-3, the illumination apparatus 1 is designed in three parts and comprises a base body 3, a cover device 11 and a carrier 19 in the form of a circuit board. The base body 3 has a slightly conical outer shape with a first end 4 that has a smaller diameter than the second end 5. Between the two ends 4, 5 runs a borehole 6 arranged concentrically with the longitudinal axis 20 of the illumination apparatus 1, with the tool receptacle 33 protruding into the borehole 6 as described above when the illumination apparatus 1 is attached to the medical handle device 30. A wall 7 in which a ring-shaped blind hole 8 is provided runs around the longitudinal axis 20 and around the borehole 6.

The part of the wall 7 that extends from the bottom 10 of the blind hole 8 up to the first end 4 of the base body 3 forms a light-emitting window 9. The light-emitting window 9 is thus an integral part designed in one piece with the base body 3 which is made of a material that is transparent for the light emitted or converted by the LEDs 2. The light-emitting window 9 ends at the first end 4 in a light-emitting surface 18 which is designed as a flat surface in FIGS. 1-3 on which an optical element, e.g., a converging lens, for example, may be mounted if necessary. As an alternative, the light-emitting surface 18 may itself function as an optical element, i.e., it may be shaped as a converging lens, for example. The base body 3 is made of plastic, in particular polyphenylsulfone, polyethersulfone, polycarbonate or polyamide or it may be made of glass. The base body 3 in FIG. 1 has a length of approximately 5-10 mm, an outside diameter of approximately 11 mm on the first end 4 and an inside diameter of the bore 6 at the first end 4 of approximately 5 mm.

Four optical semiconductor components 2 in the form of light-emitting diodes (LEDs) are attached to the ring-shaped carrier 19 at regular intervals of approximately 90°. Identical LEDs or LEDs that emit different wavelengths may be used, so that on the whole an essentially white light is emitted. The carrier 19 is shaped to have a first central bore 21 and two additional smaller eccentric bores 22. As shown in FIGS. 2 and 3 in particular, the outside diameter of the carrier 19, the diameter of the bore 21 and thus the wall thickness of the ring-shaped carrier wall are of such dimensions that the carrier 19 with the LEDs 2 can be inserted into the blind hole 8. An electric contact passes through each of the bores 22 as part of the electric power supply system for supplying electric power to the LEDs 2, which are connected in series.

The cover device 11 is designed as a ring-shaped closure body 12 having a central bore 15 extending from the second end 14 to the first end 13. The tool receptacle 33 passes through the bore 15, just like it passes through the bore 21 of the carrier 19, when the illumination apparatus 1 is connected to the medical handle device 30. Two small bores 17 to receive the electric contacts of the electric power supply device are inserted into the ring-shaped wall 16 of the cover device 11. In the installed state, the bores 17 are connected to the bores 22 of the carrier 19. The cover device 11 is made of plastic, in particular polyphenylsulfone, polyethersulfone, polycarbonate or polyamide, glass or ceramic. The cover device 11 in FIG. 2 has a length of approximately 1-5 mm.

As shown in FIGS. 2 and 3, a portion of the cover device 11 is accommodated in the blind hole 8 of the base body 3. To facilitate the introduction of the cover device 11 into the blind hole 8, the first end 13 has bevels on its outside circumference and on the circumference of the bore 15. Due to a permanently tight connection of the cover device 11 with the base body 3, a hermetically sealed interior is formed from the blind hole 8 in which the LEDs 2 are arranged. The connection may be established by pressing, bonding or by means of sealing elements, e.g., O-rings or rubber rings. The connection is preferably formed by welding, especially preferably by laser welding. In the case of sealing by means of sealing elements, ring grooves may be provided in the wall 16 of the cover device 11 and/or in the walls of the blind hole 8 to receive the sealing elements.

During operation the LEDs 2 emit radiation into the hermetically sealed interior, whereby the radiation is emitted to the environment via the transparent light-emitting window 9 and the light-emitting surface 18. If necessary, additional function elements may also be present in the hermetically sealed interior to improve the light emission, e.g., conversion pastes containing luminescent pigments for converting the wavelength emitted by the optical semiconductor component or the LEDs 2, filters or reflectors for deflecting the radiation in the direction of the light-emitting window 9. These function elements are thus also protected from moisture, chemicals and other harmful environmental influences.

The illumination apparatus 1' of FIG. 3 differs from the illumination apparatus 1 in its definitely smaller overall height which is achieved by means of smaller length dimensions—based on the longitudinal axis 20—of the base body 3' and the cover device 11'. Accordingly, the light-emitting window 9' is also designed to be narrower. To nevertheless obtain a reliable encapsulation of the hermetically sealed interior comprising the blind hole 8, the wall 16 of the cover device 11' consists of a first section 16A having a smaller diameter and a second flange-like section 16B having a larger diameter. The ring shoulders 23 and 24 formed by the flange-like section 16B serve as a support for the base body 3' and in particular form an excellent connection point for welding the base body 3' to the cover device 11'.

Figure 5:
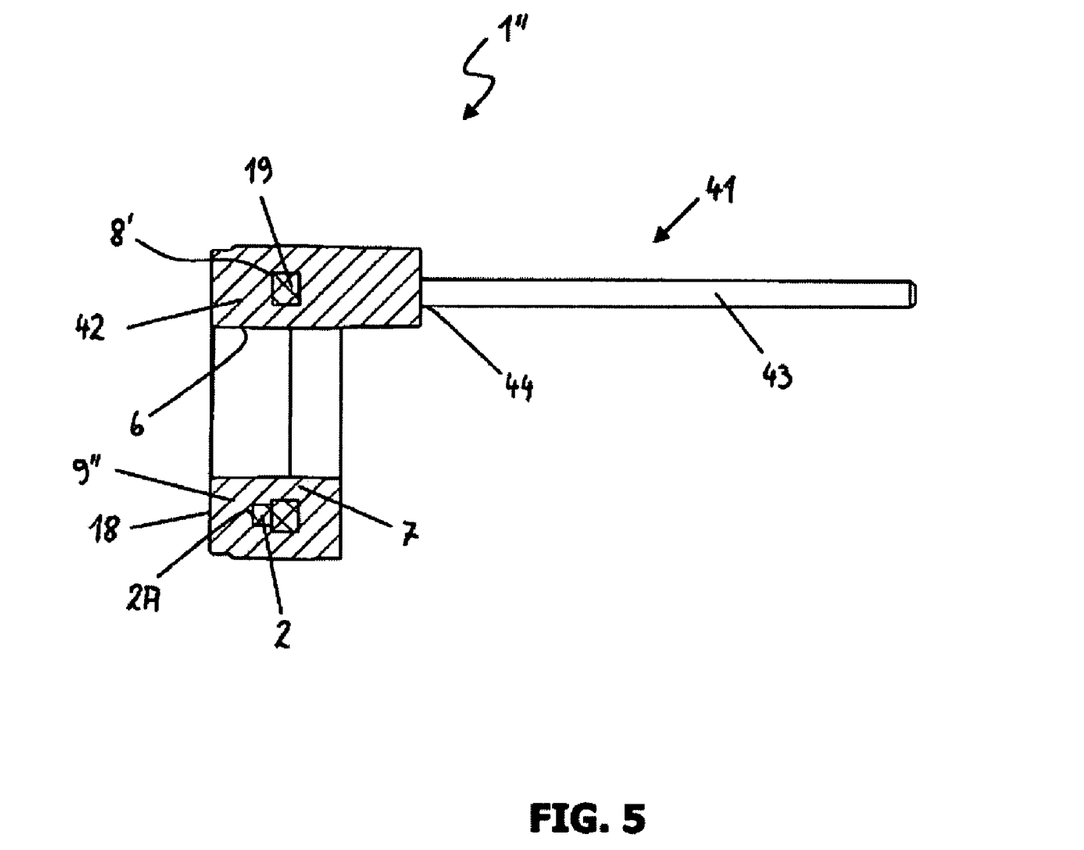
FIG. 5 shows a third exemplary embodiment of the illumination apparatus of a medical handle device.

The embodiment shown in FIG. 5 displays a casing 42 of the optical semiconductor components 2 which is designed in one piece so that there is no separation of the casing into a base body and a cover device. This also eliminates the need for connecting the base body to the cover device, so this eliminates the risk of leakage at the connecting point. Of course, however, it is also possible to manufacture the base body and the cover device as separate components made of thermoplastic material and then join them together subsequently. The design of such a two-part or multipart illumination apparatus resembles or is identical to that of illumination apparatuses 1 and 1' in FIGS. 1-3, for example.

The encasing of the components with the thermoplastic material is accomplished by liquefying the thermoplastic material, which is in solid form, in particular by heating, encasing the components with the liquid plastic and curing the thermoplastic material with the components embedded therein. The components are encased under pressure, especially preferably by means of an injection molding method.

The carrier 19 and the optical semiconductor components 2 are arranged in a receptacle 8' of the casing 42. The electric contacts 43 are accommodated in bores 44 running from one end of the casing 42 to the optical semiconductor components 2. The carrier 19, the optical semiconductor components 2 and the electric contacts 43 are tightly encased by the thermoplastic material in such a way that liquids or gases cannot penetrate up to the optical semiconductor components 2 and the carrier. Thus, the receptacle 8' is designed as a hermetically sealed interior.

The illumination apparatus 1" of FIG. 5 again comprises a ring shaped carrier 19, in particular a circuit board or a multilayer ceramic, with a central bore and a plurality of optical semiconductor components 2 arranged thereon. An electric power supply device 41 comprising two metallic pins (only one pin 43 is displayed) connects the optical semiconductor components 2 to a power source. The carrier 19, the optical semiconductor components 2 and a part of the electrical contact pins 43 are enclosed by a casing 42 made of transparent thermoplastic material. The electrical pins 43 are surrounded by a projection, which is part of the casing 42 and which projects from the otherwise cylindrical, hollow illumination apparatus 1".

The thermoplastic material forming the casing 42 preferably is a propylene random copolymer (PPR), in particular a nucleated random copolymer polypropylene, which is offered e.g. by the company Total Petrochemicals under the name PPR 9220. Of course the casing 42 may consist of other thermoplastic materials.

As FIG. 5 also shows, the thermoplastic material of the casing 42 comes in direct contact with the radiation-emitting surfaces 2A of the optical semiconductor component 2. The light-emitting window 9" is in contact with these surfaces 2A and/or the receptacle 8', ending in a planar or curved light-emitting surface 18.

According to the illumination apparatuses 1 and 1', the illumination apparatus 1" also has a bore 6 into which the tool receptacle 33 and a tool protrude when the illumination apparatus 1" is attached to the medical handle device 30. A ring-shaped wall 7 forming the casing 42 runs around the bore 6.

The present disclosure is not limited to the exemplary embodiments described here but instead comprises all possible embodiments that do not alter its principles. In particular the shape of the entire illumination apparatus or parts thereof may be variable and need not be limited to the ring-shaped, cylindrical or conical shape shown here. Depending on the available space, the desired light distribution pattern or other requirements, rectangular or polygonal shapes are also possible, for example. It should also be pointed out that the illumination apparatus need not necessarily be designed as a ring-shaped light, as shown in FIGS. 1-3 and 5, where it surrounds a treatment tool, a tool receptacle or another component and is provided with bores 6, 15, 21. An illumination apparatus according to this invention may of course also be manufactured without these bores 6, 15, 21, and an optical fiber, for example, which conducts the light to the tool-side end or to another desired light-emitting location on the medical handle device, may also be connected to the light-emitting surface 18.

What is claimed is:

1. A medical handle device having an illumination apparatus with at least one optical semiconductor component as the light source, whereby the illumination apparatus comprises:
   a base body having a first end and a second end,
   at least one blind hole arranged in the base body, extending from the second end of the base body in the direction of the first end,
   a light-emitting window formed by a part of the base body, wherein the light emitting window extends from a bottom of the blind hole to the first end of the base body,
   a cover device which is connected to the base body and together with the blind hole forms a hermetically sealed interior,
   wherein the at least one optical semiconductor component is arranged in the hermetically sealed interior and is connected to an electric power source via an electric power supply device via bores in the illumination apparatus, and wherein the base body and the cover device are made of an electrically nonconducting material, and
   wherein the illumination apparatus comprising the optical semiconductor component is arranged in or on an outer sleeve of the medical handle device.

2. The medical handle device according to claim 1, wherein the base body and the cover device are made of a sterilizable material having a melting point of more than 120° C.

3. The medical handle device according to claim 1, wherein at least a part of the cover device is accommodated in the at least one blind hole of the base body.

4. The medical handle device according to claim 1, wherein the cover device comprises a ring-shaped closure body having a first end and a second end and having an inner circumferential wall and an outer circumferential wall, whereby the ring-shaped closure body is designed with a through-bore extending from the first end to the second end, said through-bore defining the inner circumferential wall.

5. The medical handle device according to claim 1, wherein the base body is made of plastic or glass, and the cover device is made of a plastic, glass or ceramic.

6. The medical handle device according to claim 1, wherein the base body and the cover device are welded, pressed or bonded together or are joined together by sealing elements.

7. The medical handle device according to claim 1, wherein the cover device is formed by epoxy resin, silicone resins or polyamide resins.

8. The medical handle device according to claim 1, wherein the electric power supply device comprises at least one first electric contact and one second electric contact which are connected through said bores in the illumination apparatus to the at least one optical semiconductor component.

9. The medical handle device according to claim 1, wherein an inductive electric power supply device is provided with at least one first coil which is arranged in the hermetically sealed interior of the illumination apparatus and is provided with at least one second coil which is arranged outside of the hermetically sealed interior.

10. The medical handle device according to claim 9, wherein
    additional electronic components are provided between the first coil and the at least one optical semiconductor component.

11. A method for manufacturing a medical handle device having an illumination apparatus, comprising the steps:
    providing a medical handle device,
    providing an illumination apparatus having at least one optical semiconductor component as the light source, wherein the illumination apparatus additionally comprises:
       a base body having a first end and a second end,
       at least one blind hole arranged in the base body, extending from the second end of the base body in the direction of the first end,
       a light-emitting window formed by the part of the base body extending from the bottom of the blind hole to the first end of the base body,
       a cover device which is connected to the base body and together with the blind hole forms a hermetically sealed interior,
    whereby the at least one optical semiconductor component is arranged in the hermetically sealed interior and is connected to an electric power source via an electric power supply device via bores in the illumination apparatus and whereby the base body and the cover device are made of an electrically non-conducting material, and
    fastening the illumination apparatus in or on an outer sleeve of the medical handle device.

12. A method for manufacturing a medical handle device having an illumination apparatus, the illumination apparatus comprising at least one optical semiconductor component, a circuit board or a multilayer ceramic for carrying the at least one optical semiconductor component and two metallic pins for supplying electric power to the at least one optical semiconductor component, wherein the at least one optical semiconductor component is arranged on the circuit board or the multilayer ceramic so that the at least one optical semiconductor component and the circuit board or the multilayer ceramic form an illumination unit having a front side, a rear side and a circumferential side, the method for manufacturing the medical handle device comprising the steps:
    providing a medical handle device,
    encasing the illumination unit in a transparent thermoplastic, such that the front side, the rear side and the circumferential side of the illumination unit are enclosed by the transparent thermoplastic and at least a part of each of the two metallic pins project out of the transparent thermoplastic, and
    fastening the illumination apparatus in or on the medical handle device.

13. The method for manufacturing a medical handle device according to claim 12, wherein
    the illumination unit is encased by making available a solid thermoplastic, liquefying the thermoplastic and curing the thermoplastic.

14. The method for manufacturing a medical handle device according to claim 12, wherein
    the illumination unit is encased by heating the thermoplastic to a temperature of not greater than approximately 310° C.

15. The method for manufacturing a medical handle device according to claim 12, wherein
the illumination unit is arranged in a mold before the at least one optical semiconductor component is encased in the thermoplastic, and then the thermoplastic is introduced into the mold.

16. The method for manufacturing a medical handle device according to claim 15, wherein
the thermoplastic is injected into the mold under pressure.

17. The method for manufacturing a medical handle device according to claim 12, wherein
the at least one optical semiconductor component is encased by the thermoplastic in such a way that the thermoplastic either contacts at least the radiation-emitting surface of the at least one optical semiconductor component or the thermoplastic contacts the components connected to the radiation-emitting surface.

18. The method for manufacturing a medical handle device according to claim 12, wherein
the illumination unit is encased in the transparent thermoplastic in one piece.

19. A medical handle device having an illumination apparatus, the illumination apparatus comprising at least one optical semiconductor component, a circuit board or a multilayer ceramic for carrying the at least one optical semiconductor component and two metallic pins for supplying electric power to the at least one optical semiconductor component, wherein the at least one optical semiconductor component is arranged on the circuit board or the multilayer ceramic so that the at least one optical semiconductor component and the circuit board or the multilayer ceramic form an illumination unit having a front side, a rear side and a circumferential side, and wherein
the illumination unit is encased in a transparent thermoplastic, such that the front side, the rear side and the circumferential side of the illumination unit are enclosed by the transparent thermoplastic and at least a part of each of the two metallic pins project out of the transparent thermoplastic.

20. The medical handle device according to claim 19, wherein
the at least one optical semiconductor component is encased by the thermoplastic in such a way that the thermoplastic either contacts at least the radiation-emitting surface of the at least one optical semiconductor component or the thermoplastic contacts components connected to the radiation-emitting surface.

21. The medical handle device according to claim 19, wherein
the casing formed by the thermoplastic is designed in one piece.

22. The medical handle device according to claim 19, wherein
the casing formed by the thermoplastic is designed in two or more parts.

23. The medical handle device according to claim 19, wherein
the casing formed by the transparent thermoplastic comprises:
a base body having a first end, a second end and at least one receptacle, wherein the at least one receptacle extends from the second end of the base body in the direction of the first end,
a light-emitting window that is formed by the part of the base body that extends from the at least one receptacle to the first end of the base body,
a cover device which is connected to the base body in such a way that the at least one receptacle forms a hermetically sealed interior,
and wherein the at least one optical semiconductor component is arranged in the hermetically sealed interior.

24. The medical handle device according to claim 23, wherein
at least a portion of the cover device is accommodated in the at least one receptacle of the base body.

25. The medical handle device according to claim 23, wherein
the cover device comprises a closure body having a first end and a second end, whereby the closure body is preferably designed with a bore extending from the first end to the second end and with a wall enclosing the bore.

26. The medical handle device according to claim 19, wherein
the casing of the illumination apparatus is manufactured from a thermoplastic whose resoftening point is above 120° C.

27. The medical handle device according to claim 19, wherein
the two metallic pins are connected through bores in the transparent thermoplastic to the at least one optical semiconductor component.

28. The medical handle device according to claim 19, comprising
an inductive electric power supply device having at least one first coil which is arranged in the transparent thermoplastic encasing the illumination unit and at least one second coil which is arranged outside of the transparent thermoplastic encasing the illumination unit.

29. The medical handle device according to claim 28, wherein
additional electronic components are provided between the first coil and the at least one optical semiconductor component.

* * * * *